(12) United States Patent

Kimura et al.

(10) Patent No.: US 6,919,452 B1
(45) Date of Patent: Jul. 19, 2005

(54) DIAMINOSTILBENE DERIVATIVES

(75) Inventors: Keizo Kimura, Minami-ashigara (JP); Yoshiharu Yabuki, Minami-ashigara (JP); Yasufumi Nakai, Minami-ashigara (JP)

(73) Assignee: Fuji Photo Film Co., LTD, Kanagawa (JP)

( * ) Notice: Subject to any disclaimer, the term of this patent is extended or adjusted under 35 U.S.C. 154(b) by 0 days.

(21) Appl. No.: 09/678,330

(22) Filed: Oct. 3, 2000

(51) Int. Cl.$^7$ .................. C07D 251/68; C09K 11/06
(52) U.S. Cl. ................ 544/193.2; 252/301.21; 252/301.23; 427/411; 427/412; 427/158
(58) Field of Search ...................... 544/193.2

(56) References Cited

U.S. PATENT DOCUMENTS

| | | | | |
|---|---|---|---|---|
| 3,193,548 A | * | 7/1965 | Crounse et al. .......... | 544/193.2 |
| 3,309,363 A | * | 3/1967 | Buell ...................... | 544/193.2 |
| 5,395,742 A | * | 3/1995 | Deguchi et al. ......... | 544/193.2 |

* cited by examiner

Primary Examiner—Venkataraman Balasubramanian
(74) Attorney, Agent, or Firm—Birch, Stewart, Kolasch & Birch, LLP

(57) ABSTRACT

The following 4,4'-bis(1,3,5-triazinylamino)stilbene-2,2'-disulfonic acid derivative is well soluble in water:

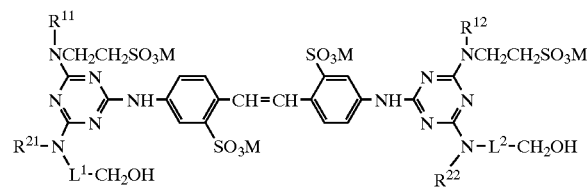

in which each of $R^{11}$ and $R^{12}$ is hydrogen, or a specifically substituted or unsubstituted alkyl group; each of $R^{21}$ and $R^{22}$ is hydrogen, a specifically substituted or unsubstituted alkyl group, a specifically substituted or unsubstituted aryl group; M is hydrogen, alkali metal, alkaline earth metal, ammonium, or pyridinium.

7 Claims, No Drawings

DIAMINOSTILBENE DERIVATIVES

FIELD OF THE INVENTION

The present invention relates to a 4,4'-bis(1,3,5-triazinylamino)stilbene-2,2'-disulfonic acid derivative which is favorably employable in an aqueous fluorescent brightening solution, an aqueous photographic silver halide emulsion, an aqueous solution for processing a photographic silver halide-containing material. The invention further relates to use of the 4,4'-bis(1,3,5-triazinylamino)stilbene-2,2'-disulfonic acid derivative for brightening a variety of materials with fluorescence.

BACKGROUND OF THE INVENTION

Tamehiko Noguchi describes in Journal of Society of Organic Synthetic Chemistry (Yuki Gosei Kagaku Kyoukaishi), vol. 19, p. 920 (1961) and vol. 20, p. 64 (1962) that 4,4'-bis(1,3,5-triazinylamino)stilbene-2,2'-disulfonic acid derivatives are useful as fluorescent brightening agents.

U.S. Pat. No. 2,875,058, No. 2,933,390, and No. 2,945,762 describe 4,4'-bis(1,3,5-triazinyl-amino)stilbene-2,2'-disulfonic acid derivatives are employable as additives for a photographic silver halide emulsion.

German Patent (DE) No. 1,945,316 discloses 4,4'-bis-(1,3,5-triazinylamino)stilbene-2,2'-disulfonic acid derivatives which show high fluorescent brightening effect on cellulose fibers. The disclosed derivatives have a sulfoethylamine substituent group on the 2-position of its triazine ring and additionally a morpholine or alkanolamine substituent group on the 4-position. Examples of the alkanolamines are monoethanolamine, methylethanolamine, diethanolamine, isopropanolamine, and diisopropanolamine.

The 4,4'-bis(1,3,5-triazinylamino)stilbene-2,2'-disulfonic acid derivatives to be employed in the form of aqueous solutions such as photographic silver halide emulsions and aqueous solutions for processing photographic silver halide-containing material are preferably well soluble in water or an aqueous solution. In more detail, the derivatives should be rapidly dissolved in an aqueous medium and then should be hardly deposited during the storage of the aqueous solution.

Japanese Patent Provisional Publications No. 6-329,936 and No. 6-332,127 disclose 4,4'-bis(1,3,5-tri-azinylamino) stilbene-2,2'-disulfonic acid derivatives which are employable as fluorescent brightening agents for an aqueous solution for processing photographic silver halide material. The disclosed derivatives have high solubility in the aqueous solution and are hardly deposited even when the processing solution is kept at low temperatures. The latter 6-332,127 publication indicates that a preferred compound is such derivative that the triazine ring is substituted on its 2-position with ethylamine having a sodium sulfonate salt [therefore, four sodium sulfonate groups are introduced into the derivative] and further substituted on its 4-position with an alkanolamine (e.g., 2-methyethanolamine).

SUMMARY OF THE INVENTION

According to the studies of the present inventors, the known 4,4'-bis(1,3,5-triazinylamino)stilbene-2,2'-disulfonic acid derivatives do not show satisfactory solubility in an aqueous medium from the viewpoints of practical use of the fluorescent brightening agent.

It is an object of the present invention to provide 4,4'-bis(1,3,5-triazinylamino)stilbene-2,2'-disulfonic acid derivatives which show increased solubility in an aqueous medium.

As a result of further studies performed by the inventors, it has been discovered that the desired high solubility is attained by introducing into the 4-position of the triazine ring of the 4,4'-bis(1,3,5-triazinyl-amino)stilbene-2,2'-disulfonic acid derivative an amino group having an alkylene substituent of 2 to 8 carbon atoms in which the alkylene substituent has a hydroxyl group or a hydroxyalkyl group of 1 to 3 carbon atoms as a substituent or has an intervening ether bonding.

Accordingly, the present invention resides in a 4,4'-bis(1,3,5-triazinylamino)stilbene-2,2'-disulfonic acid derivative having the following formula (1):

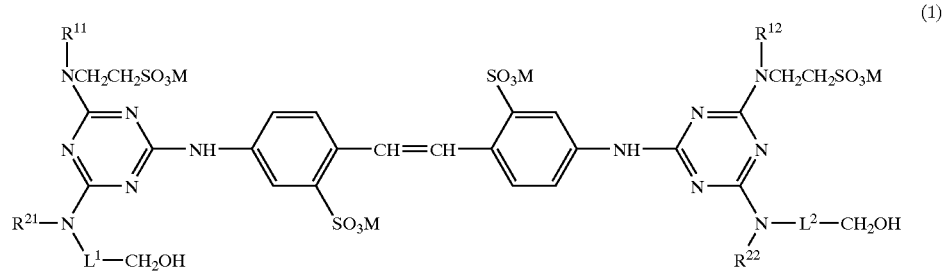

(1)

in which
each of $R^{11}$ and $R^{12}$ independently is a hydrogen atom, an alkyl group having 1 to 20 carbon atoms, or an alkyl group having 1 to 20 carbon atoms which has one or more substituents selected from the group consisting of hydroxyl, sulfo, and alkoxy;

$R^{21}$ is a hydrogen atom, an alkyl group having 1 to 20 carbon atoms, an alkyl group having 1 to 20 carbon atoms which has one or more substituents selected from the group consisting of hydroxyl, sulfo, and alkoxy, an aryl group having 6 to 20 carbon atoms, an aryl group having 6 to 20 carbon atoms which has one or more substituents selected from the group consisting of hydroxyl, carboxyl, alkyl, or alkoxy, or a group represented by the formula of -$L^1$-$CH_2OH$ wherein $L^1$ is an alkylene group having 2 to 8 carbon atoms which has one or more substituents selected from the group consisting of hydroxyl and hydroxylalkyl having 1 to 3 carbon atoms or which has an intervening ether bonding;

$R^{22}$ is a hydrogen atom, an alkyl group having 1 to 20 carbon atoms, an alkyl group having 1 to 20 carbon atoms which has one or more substituents selected from the group consisting of hydroxyl, sulfo, and alkoxy, an aryl group having 6 to 20 carbon atoms, an aryl group having 6 to 20 carbon atoms which has one or more substituents selected from the group consisting of hydroxyl, carboxyl, alkyl, or alkoxy, or a group represented by the formula of -$L^2$-$CH_2OH$ wherein $L^2$ is an alkylene group having 2 to 8 carbon atoms which has one or more substituents selected from the group consisting of hydroxyl and hydroxylalkyl having 1 to 3 carbon atoms or which has an intervening ether bonding; and M is a hydrogen atom, an alkali metal atom, an alkaline earth metal atom, ammonium group, or pyridinium group.

The 4,4'-bis(1,3,5-triazinylamino)stilbene-2,2'-disulfonic acid derivatives of the invention is included in the general formula (SR) of the diaminostilbene compound for fluorescent brightening agent which is disclosed in the aforementioned Japanese Patent Provisional Publication No. 6-332127. However, the specifically defined 4,4'-bis(1,3,5-triazinylamino)stilbene-2,2'-disulfonic acid derivatives of the invention are not described in the publication.

The present invention further resides in an aqueous solution containing a 4,4'-bis(1,3,5-triazinylamino)-stilbene-2,2'-disulfonic acid derivative of the above-mentioned formula (1).

The invention furthermore resides in a method of brightening a surface of material with fluorescence which comprises applying a 4,4'-bis(1,3,5-triazinylamino)-stilbene-2,2'-disulfonic acid derivative of the formula (1) onto the surface of material.

DETAILED DESCRIPTION OF THE INVENTION

The 4,4'-bis(1,3,5-triazinylamino)stilbene-2,2'-disulfonic acid derivatives of the invention is represented, as mentioned above, by the following formula (1):

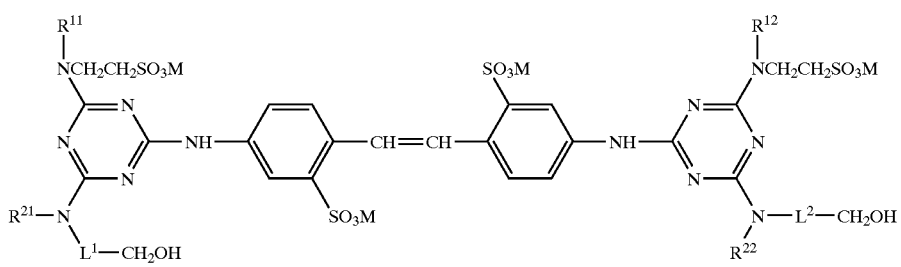

In the formula (1), an alkyl group for $R^{11}$ and $R^{12}$ has 1 to 20 carbon atoms, preferably 1 to 8 carbon atoms, more preferably 1 to 4 carbon atoms. The alkyl group can be a straight chain alkyl group, a branched chain alkyl group, or a cyclic alkyl group. The alkyl group can have one or more substituent groups. Examples of the substituent groups include a hydroxyl group, a sulfo group, and an alkoxy group. The alkoxy group preferably has such alkyl group as mentioned above.

Examples of the alkyl groups for $R^{11}$ and $R^{12}$ include methyl, ethyl, n-propyl, isopropyl, n-octyl, 2-hydroxy-ethyl, 3-hydroxypropyl, 2-hydroxypropyl, 2-sulfoethyl, 2-methoxyethyl, 2-(2-hydroxyethoxy)ethyl, 2-[2-(2-hydroxy-ethoxy)ethoxy]ethyl, and 2-(2-[2-(2-hydroxyethoxy)-ethoxy]ethoxy) ethyl.

Each of $R^{11}$ and $R^{12}$ preferably is hydrogen, methyl, ethyl, n-propyl, n-butyl, or 2-sulfoethyl, and more preferably hydrogen, methyl, ethyl, or 2-sulfoethyl. Most preferred is hydrogen or atom.

Examples of the alkyl groups for $R^{21}$ and $R^{22}$ are those described hereinbefore for $R^{11}$ and $R^{12}$. Preferred examples of $R^{21}$ and $R^{22}$ include hydrogen, methyl, ethyl, n-propyl, isopropyl, 2-hydroxyethyl, 3-hydroxypropyl, 2-hydroxypropyl, 2,3-dihydroxypropyl, 2-sulfoethyl, 2-(2-hydroxyethoxy)ethyl, and 2-[2-(2-hydroxyethoxy)ethoxy]ethyl. More preferred examples include hydrogen, methyl, ethyl, isopropyl, 2-hydroxyethyl, 2-hydroxypropyl, 3-hydroxypropyl, 2,3-dihydroxpropyl, and 2-(2-hydroxyethoxy)ethyl. Most preferred are hydrogen and methyl.

The aryl group for $R^{21}$ and $R^{22}$ has 6 to 20 carbon atoms, preferably 6 to 10 carbon atoms, more preferably 6 to 8 carbon atoms. The aryl group can have one or more substituents. Examples of the substituents include a hydroxyl group, a carboxyl group, an alkyl group, and an alkoxy group. The alkyl group and alkoxy group of the substituent can be the same as those described hereinbefore for $R^{11}$ and $R^{12}$. Examples of the substituted and unsubstitued aryl groups for $R^{21}$ and $R^{22}$ include phenyl, naphthyl, 4-hydroxyphenyl, 3,5-dicarboxyphenyl, 4-methoxyphenyl, and 3-isopropylphenyl. The aryl group preferably is phenyl or 4-hydroxyphenyl.

The alkylene group for $L^1$ and $L^2$ is an alkylene group having 2 to 8 carbon atoms which has, as a substituent, a hydroxyl group or a hyroxyalkyl group having 1 to 3 carbon atoms. Otherwise, the alkylene group has an ether bonding which intervenes the alkylene chain at an optional position.

Preferred examples of the alkylene group for $L^1$ and $L^2$ include those of the following formulas 1) to 5):

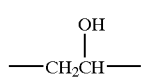

1)

2)

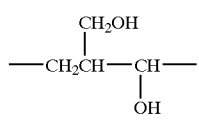

3)

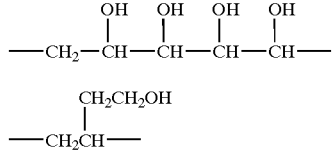

4)

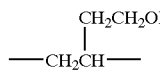

5)

More preferred are those of the above-mentioned formulas 1) to 4), namely, alkylene groups having one or more hydroxyl substituent groups. Most preferred are those of the formulas 1) and 4).

Other preferred examples of the alkylene group for $L^1$ and $L^2$ include that represented by the following formula (2):

in which n is an integer of 1 to 3, preferably 1 or 2. Most preferably, n is 1.

In the formula (1), M is a hydrogen atom, an alkali metal atom, an alkaline earth metal atom, ammonium group, or pyridinium group. Examples of the alkali metal atoms include Li, Na, K, Rb, Cs, and Fr. Examples of the alkaline earth metal atoms include Ca, Sr, Ba, and Ra. Preferred are Na and K. Examples of the ammonium groups include triethylammonium and tetrabutylammonium.

Representative examples of the formula (1) of the invention are illustrated below:

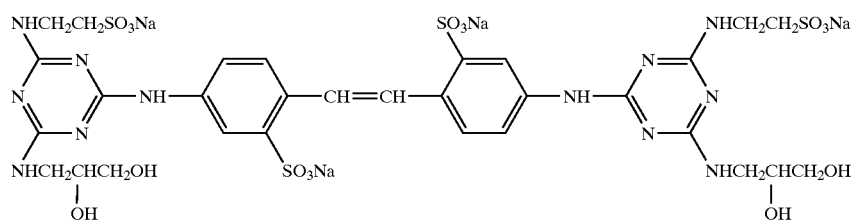

I-1

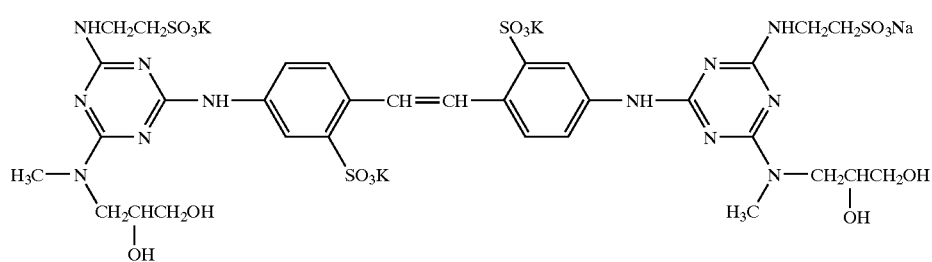

I-2

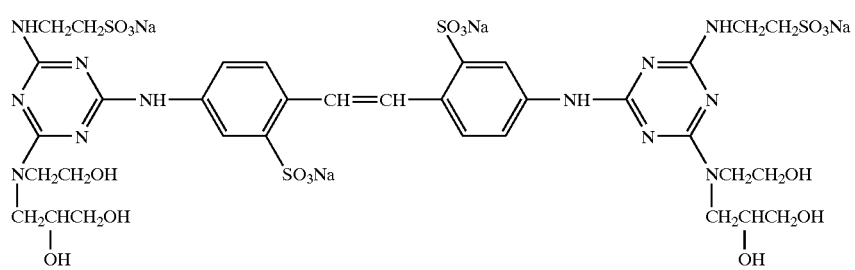

I-3

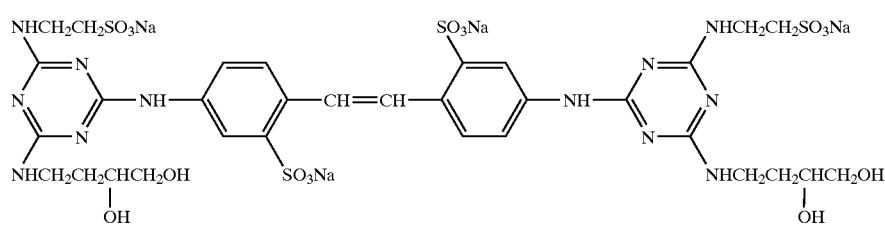

I-4

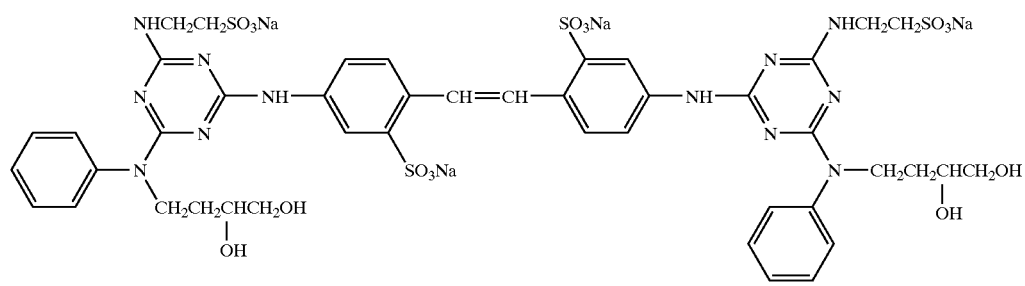

I-5

-continued
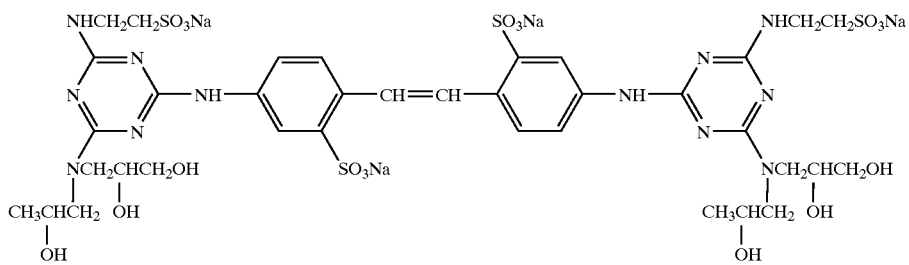
I-6
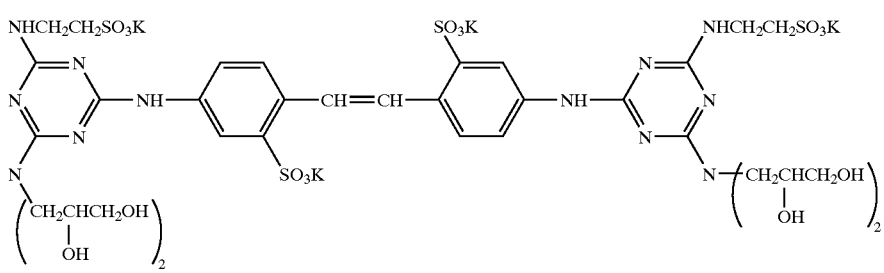
I-7
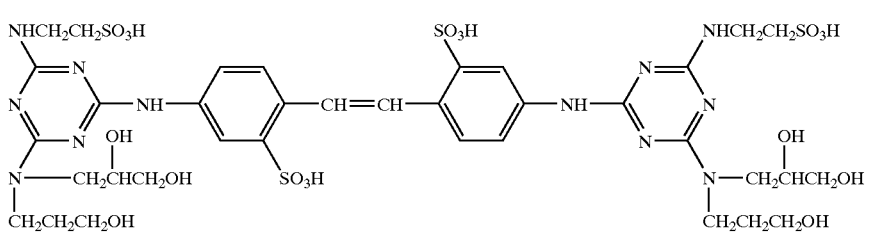
I-8
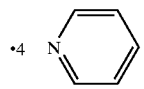
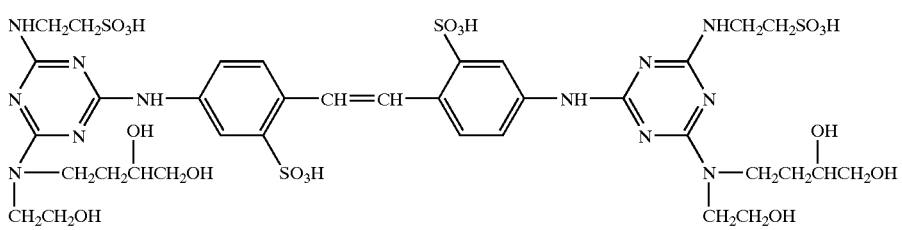
I-9
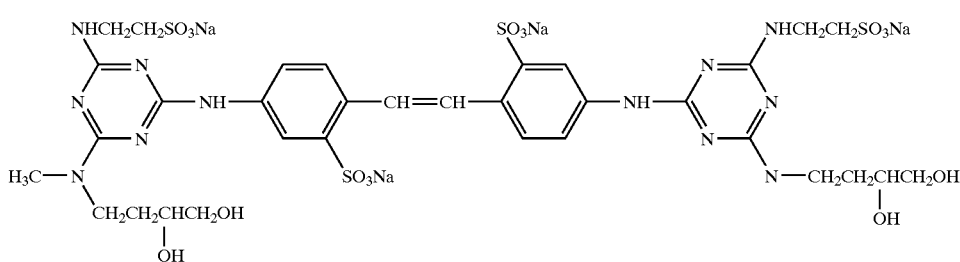
I-10
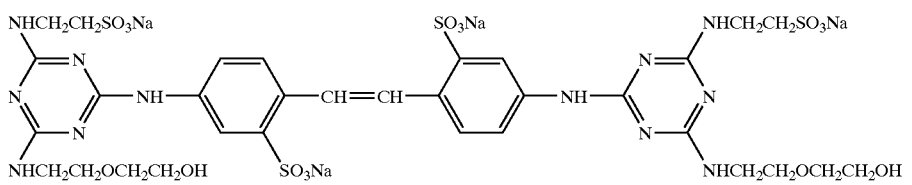
I-11

-continued
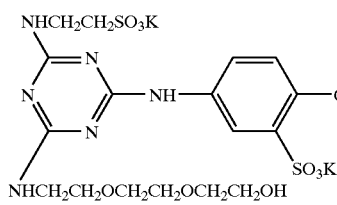 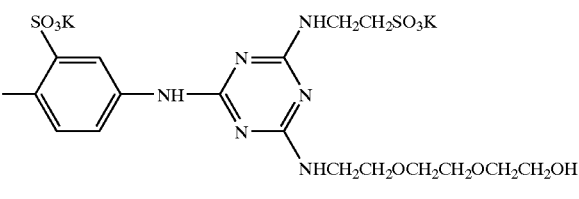
I-12
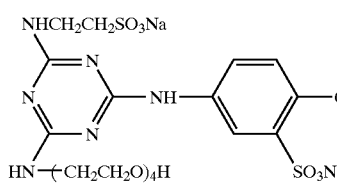 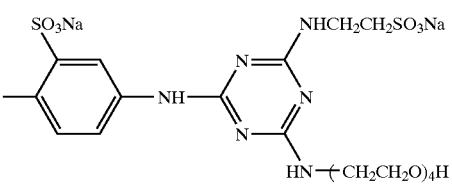
I-13
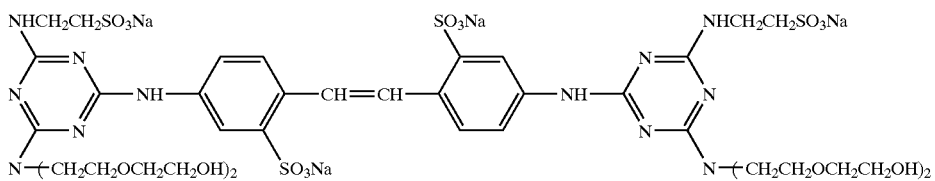
I-14
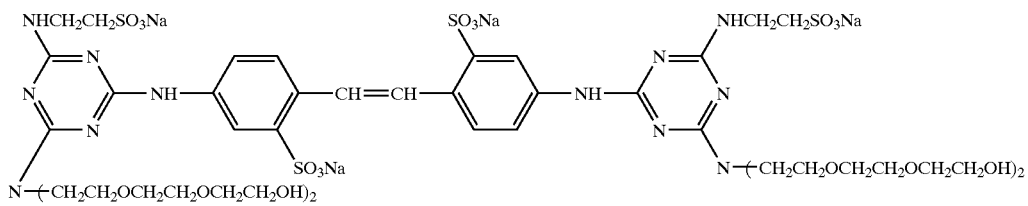
I-15
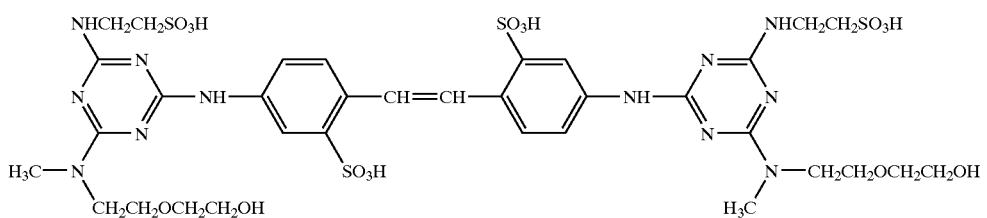
I-16
·4N(CH₃)₃
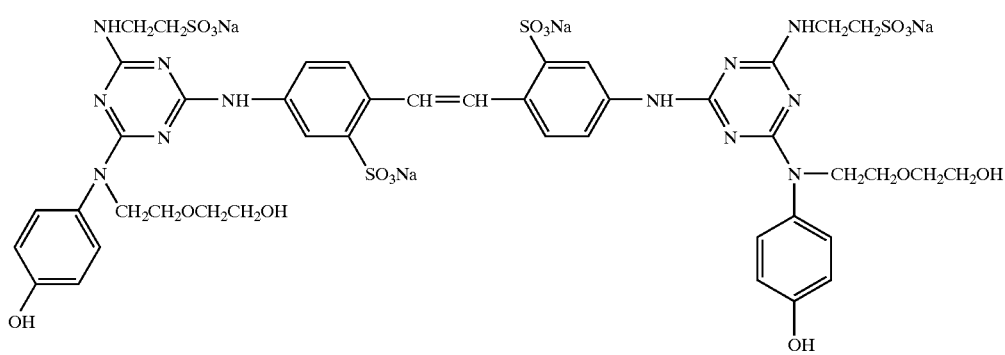
I-17
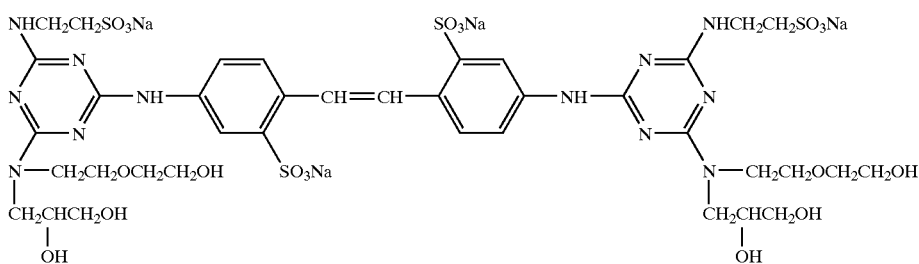
I-18

-continued
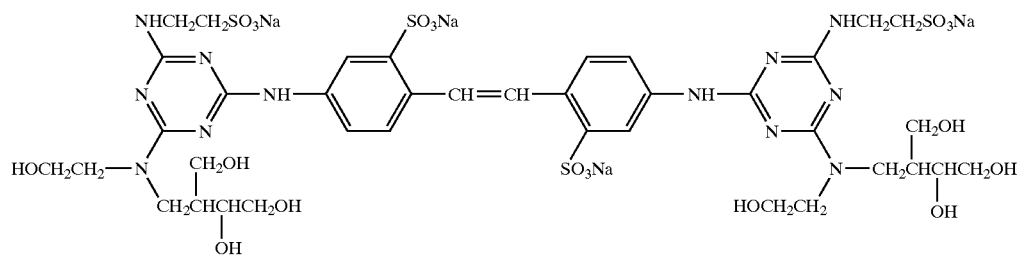
I-19
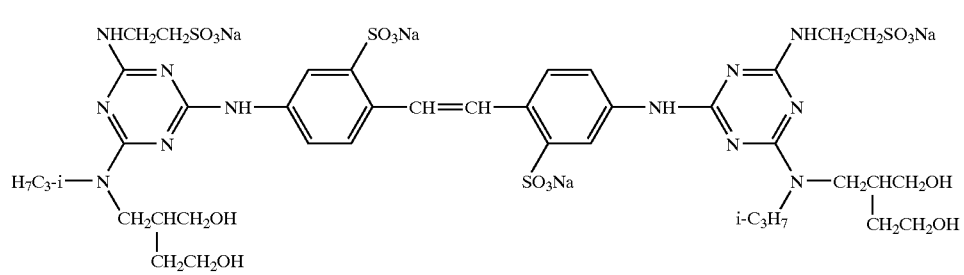
I-20
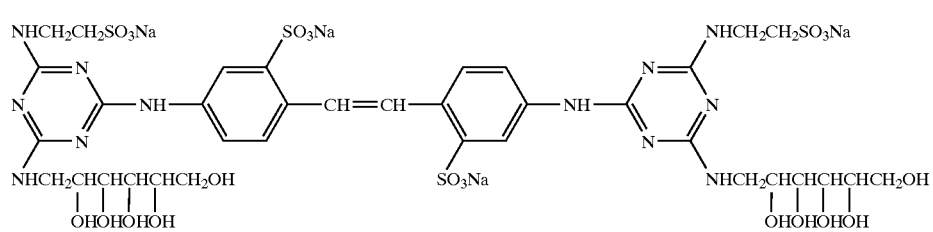
I-21
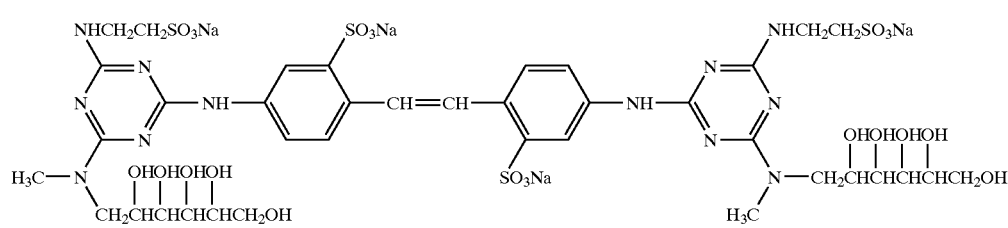
I-22
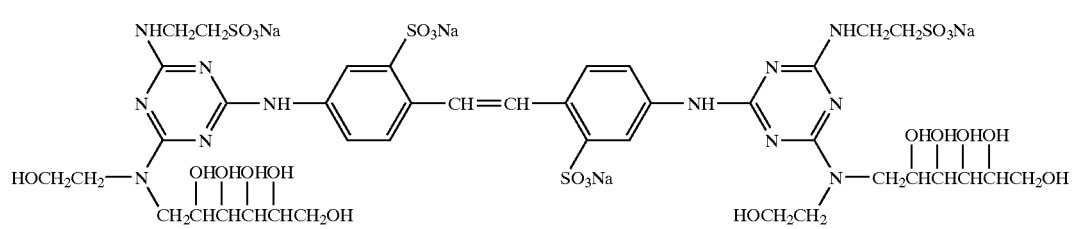
I-23
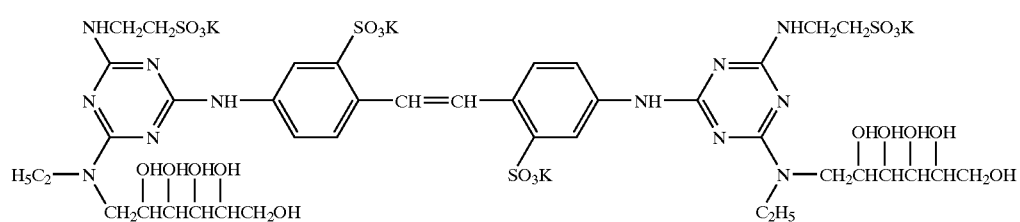
I-24

-continued
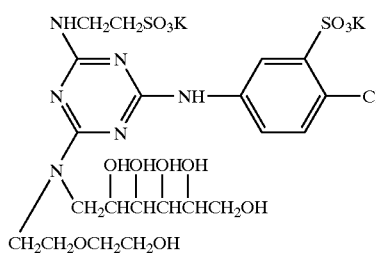 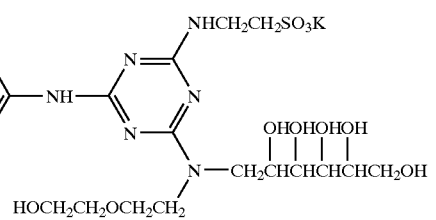
I-25
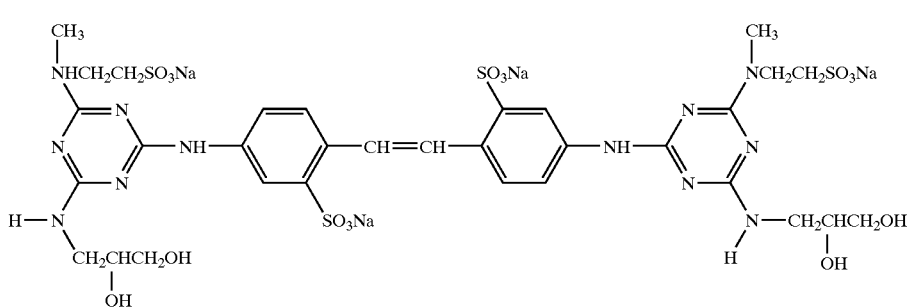
I-26
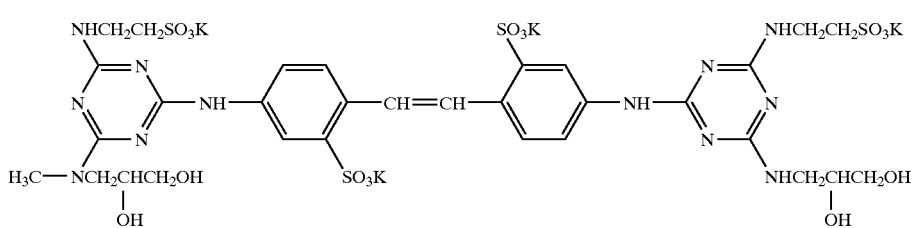
I-27
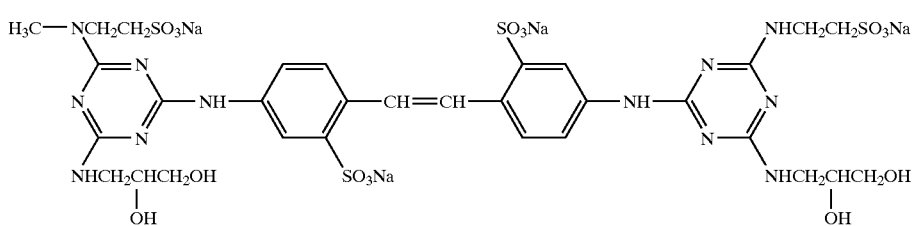
I-28
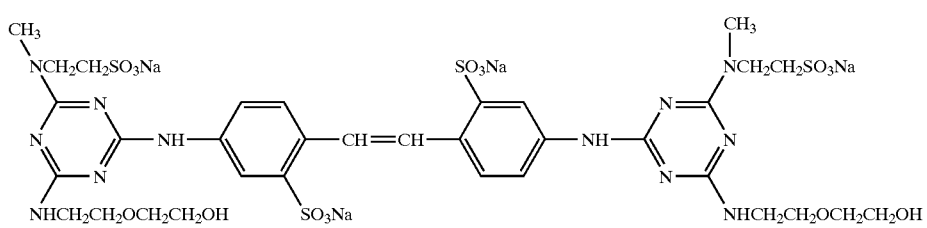
I-29
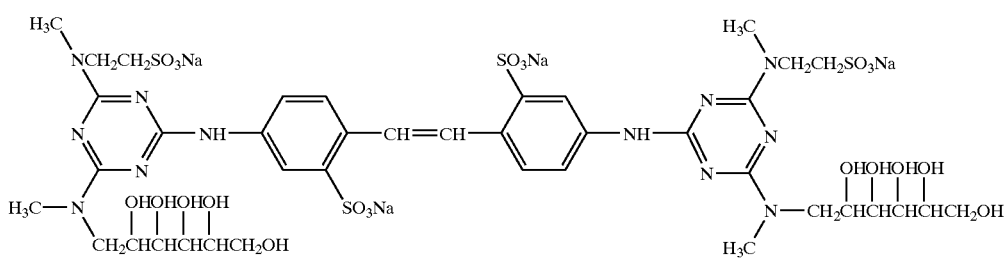
I-30

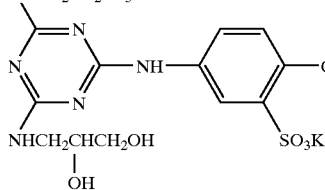
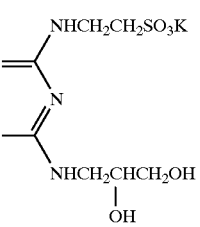

I-31

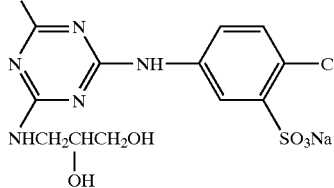
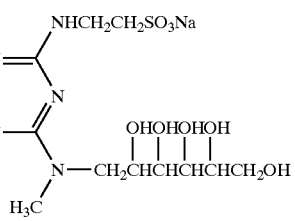

I-32

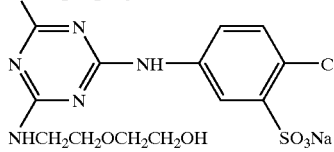
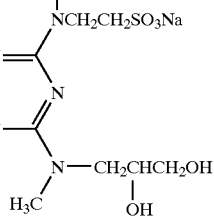

I-33

When the alkylene group for $L^1$ or $L^2$ of the formula (1) has a hydroxyl or hydroxyalkyl substituent and contains in its structure two or more asymmetric carbon atoms to which the substituent is attached, there are a plurality of stereoisomers having the same formula. Any of the isomers can be employed singly or in combination.

The 4,4'-bis(1,3,5-triazinylamino)stilbene-2,2'-disulfonic acid derivative of the formula (1) can be prepared by referring to the descriptions of Journal of Society of Organic Synthetic Chemistry, vol. 17, page 528 (1959) [written by Hirotsugu Matsui] and Japanese Patent No. 2,618,748.

In more detail, the compound of the formula (1) can be prepared by the steps of reacting a diaminostilbene derivative with cyanuric chloride, reacting the resulting 4,4'-bistriazinylaminostilbene derivative with taurine, and finally reacting the resulting product with hydroxyalkylamine. Otherwise, a process starting from a dialkylaminostilbene derivative can be adopted.

The reaction can be performed in a solvent such as water or an organic solvent (e.g., alcohol, ketone, ether or amide). Water and water-miscible organic solvents are preferred. The reaction solvent can be a mixture of appropriate solvents. Preferred is an aqueous acetone solvent. Generally, a base is employed in the reaction. Examples of the bases include organic bases such as triethylamine, pyridine, and 1,8-diazabicyclo[5,4,0]-7-undecene, and inorganic bases such as sodium hydroxide, potassium hydroxide, sodium carbonate, potassium carbonate, sodium hydrogen carbonate, and sodium hydride. The inorganic bases such as sodium hydroxide, potassium hydroxide, sodium carbonate and potassium carbonate are preferably employed. The reaction is generally performed at a temperature in the range of −20° C. to 120° C., preferably −10° C. to 90° C. In more detail, the reaction in the first step is preferably performed at a temperature of −10° C. to 10° C.; the reaction in the second step is preferably performed at a temperature of 0° C. to 40° C.; and the reaction in the third is preferably performed at a temperature of 50° C. to 90° C.

The present invention is further described by the following non-restricting examples.

EXAMPLE 1

The aforementioned compound (I-1) of the invention was prepared according to the following scheme:

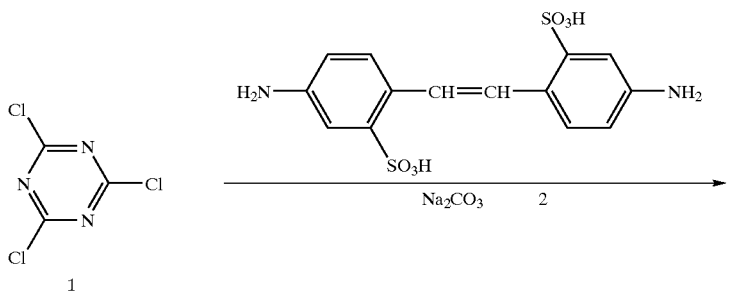

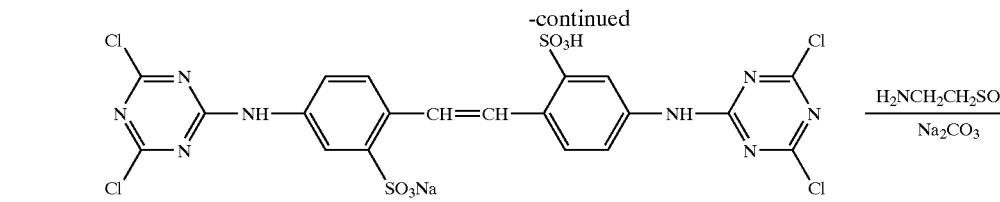

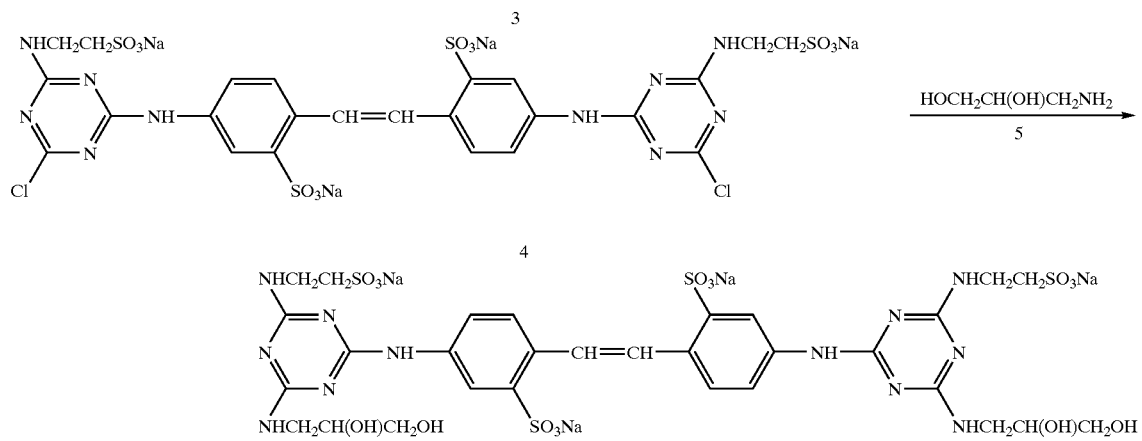

Compound (I-1)

1) Preparation of Compound 3

In a three-necked flask were placed 103.5 g of Compound 1 and 680 mL of acetone. The content was chilled to −5° C. by placing the flask in an ice-acetone bath. To the chilled content was dropwise added under stirring an aqueous solution of 101.9 g of Compound 2 and 58.3 g of sodium carbonate in 960 mL of water for a period of one hour. The temperature of the flask content increased to −1° C. After the dropwise addition was complete, the ice-acetone bath was removed, and the flask content was further stirred for one hour. The precipitated crystalline product was collected on filter by suction, to obtain the desired Compound 3. Thus obtained product was submitted to the next step without drying and purifying.

2) Preparation of Compound 4

In a three-necked flask were placed the Compound 3 obtained above and 1.9 L of water. The content was stirred on a water bath, and to the stirred content was added 68.8 g of taurine. Further, an aqueous solution of 58.3 g of sodium carbonate in 275 mL of water was dropwise added for a period of one hour under stirring. After the dropwise addition was complete, the water bath was removed and the stirring was continued for 3 hours. To the stirred content was added 550 g of sodium chloride, and the stirred is continued for one hour. The precipitated crystalline product was collected on filter by suction, to obtain the desired Compound 4. Thus obtained product was submitted to the next step without drying and purifying.

3) Preparation of the Compound (I-1)

In a three-necked flask were placed the Compound 4 obtained above and 825 mL of water. The content was stirred at room temperature, and to the stirred content was dropwise added 125.3 g of Compound 5 at room temperature, while the stirring was continued. After the dropwise addition was complete, the content was stirred at an inner temperature of 85° C. for 3 hours. The reaction mixture was concentrated in a rotary evaporator. When the residual content reduced to approximately 800 mL, a crystalline product precipitated and the concentration procedure was stopped. The content was then stirred with chilling with ice, and the precipitated crystalline product was collected on filter by suction. To thus obtained crystalline product was added 1.5 L of methanol, and the resulting mixture was stirred for one hour under reflux. The reaction mixture was cooled to room temperature, and subjected to filtration using suction, to obtain 206.0 g (yield: 72%) of the desired Compound (I-1).

$\lambda_{max}(H_2O) = 346.3$ nm ($\epsilon = 4.83 \times 10^4$)

The obtained product of Compound (I-1) had a purity of 96.0% (determined by liquid chromatography).

The liquid chromatography was carried out under the following conditions:

Column: TSK-gel ODS-80 (available from Toso Co., Ltd.)

Eluents:
  Eluent A (20 mL of PIC A reagent, available from Waters Corp., was added to 1 L of water)
  Eluent B (20 mL of PIC A reagent was added to a mixture of 800 mL of methanol and 200 mL of water)
  Eluent A/Eluent B=50/50 (0 min.)–0/100 (35 min.)

Detecting wavelength: 346 nm

The purity was determined from a peak area of the chromatographic chart.

EXAMPLE 2

The aforementioned compound (I-4) of the invention was prepared according to the following scheme:

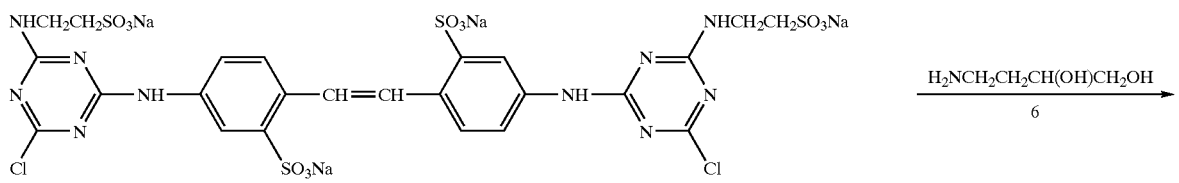

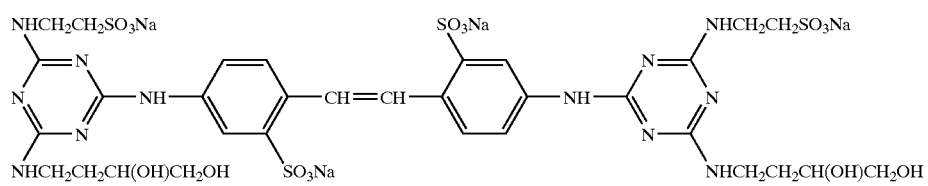

Compound (I-4)

In a three-necked flask were placed Compound 4 which had been prepared in the same manner as in Example 1 (i.e., same scale and same synthetic process) and 825 mL of water. The content was stirred at room temperature, and to the stirred content was dropwise added 144.6 g of Compound 6 at room temperature for 10 minutes, while the stirring was continued. After the dropwise addition was complete, the content was stirred at an inner temperature of 85° C. for 3 hours. The reaction mixture was concentrated in a rotary evaporator. When the residual content reduced to approximately 900 mL, a crystalline product precipitated and the concentration procedure was stopped. The content was then stirred with chilling with ice, and the precipitated crystalline product was collected on filter by suction. To thus obtained crystalline product was added 1.5 L of methanol, and the resulting mixture was stirred for one hour under reflux with heating. The reaction mixture was cooled to room temperature, and subjected to filtration using suction, to obtain 216.5 g (yield: 78%) of the desired Compound (I-4)

$\lambda_{max}(H_2O)=346.5$ nm ($\epsilon=4.77\times10^4$)

The obtained product of Compound (I-4) had a purity of 94.4% (determined by liquid chromatography which was performed in the same manner as in Example 1).

EXAMPLE 3

The aforementioned compound (I-11) of the invention was prepared according to the following scheme:

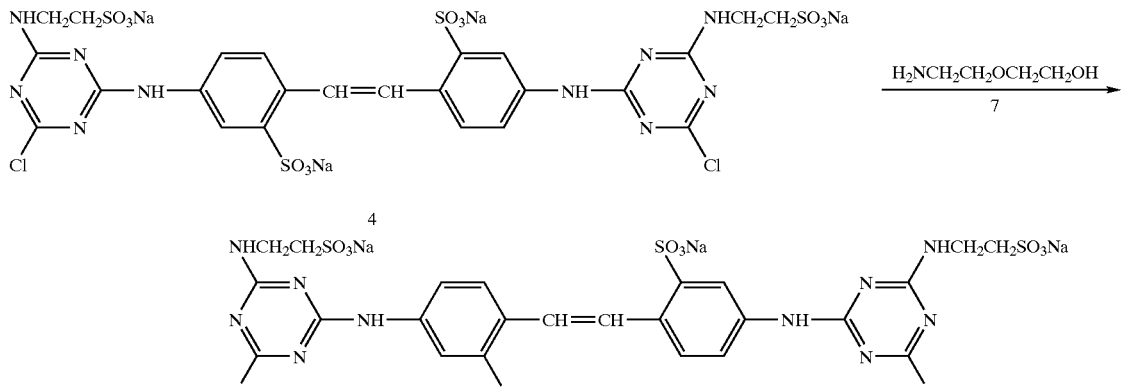

Compound (I-11)

In a three-necked flask were placed Compound 4 which had been prepared in the same manner as in Example 1 (i.e., same scale and same synthetic process) and 825 mL of water. The content was stirred at room temperature, and to the stirred content was dropwise added 144.4 g of Compound 7 at room temperature for 10 minutes, while the stirring was continued. After the dropwise addition was complete, the content was stirred at an inner temperature of 85° C. for 3 hours. The reaction mixture was concentrated in a rotary evaporator. When the residual content reduced to approximately 800 mL, a crystalline product precipitated and the concentration procedure was stopped. The content was then stirred with chilling with ice, and the precipitated crystalline product was collected on filter by suction. To thus obtained crystalline product was added 1.5 L of methanol, and the resulting mixture was stirred for one hour under reflux with heating. The reaction mixture was cooled to room temperature, and subjected to filtration using suction, to obtain 249.7 g (yield: 85%) of the desired Compound (I-11).

$\lambda_{max}(H_2O)=354.5$ nm ($\epsilon=4.92\times10^4$)

The obtained product of Compound I-11 had a purity of 97.3% (determined by liquid chromatography which was performed in the same manner as in Example 1).

EXAMPLE 4

The aforementioned compound (I-22) of the invention was prepared according to the following scheme:

was then stirred with chilling with ice, and the precipitated crystalline product was collected on filter by suction. To thus obtained crystalline product was added 1.5 L of methanol, and the resulting mixture was stirred for one hour under reflux with heating. The reaction mixture was cooled to room temperature, and subjected to filtration using suction, to obtain 302.9 g (yield: 88%) of the desired Compound (I-22).

$\lambda_{max}(H_2O)=348.6$ nm ($\epsilon=4.36\times10^4$)

The obtained product of Compound (I-22) had a purity of 96.1% (determined by liquid chromatography which was performed in the same manner as in Example 1).

EXAMPLES 5 AND 6

The aforementioned Compound (I-2) and compound (I-12) were prepared in manner similar to those described in Examples 1 to 4.

EXAMPLE 7

Compounds I-1, I-2, I-4, I-11, I-12, and I-22 obtained above, and the Comparison Compounds a, b, c and d were subjected to evaluation of solubility in water.

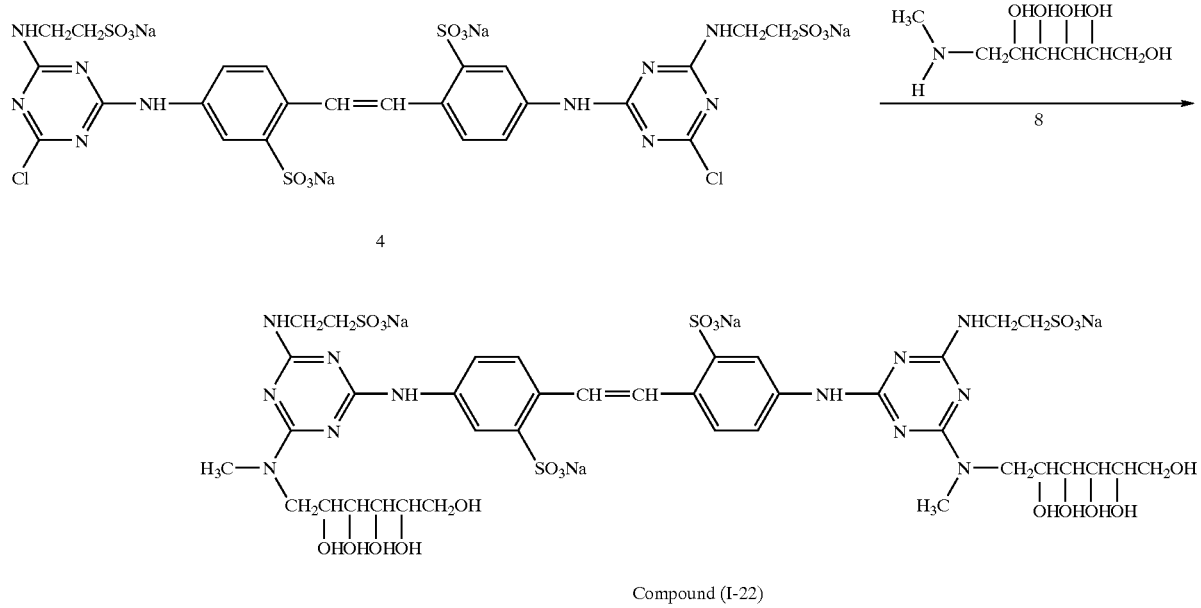

Compound (I-22)

In a three-necked flask were placed Compound 4 which had been prepared in the same manner as in Example 1 (i.e., same scale and same synthetic process) and 825 mL of water. The content was stirred at room temperature, and to the stirred content was dropwise added 268.5 g of Compound 8 at room temperature for 10 minutes, while the stirring was continued. After the dropwise-addition was complete, the content was stirred at an inner temperature of 85° C. for 3 hours. The reaction mixture was concentrated in a rotary evaporator. When the residual content reduced to approximately 900 mL, a crystalline product precipitated and the concentration procedure was stopped. The content Water (100 mL) was added to 20 g of each sample, and the mixture was placed on a warm bath (at 40° C.), and stirred using a nagnetic stirrer, so that the added sample was dissolved in the warm water. Then, the obtained aqueous solution was placed on an ice bath under stirring.

The conditions of the aqueous mixture in the dissolving procedure and the aqueous solution on the ice bath were observed for evaluating solubility in water at 40° C. and 0° C. The results are seen in the following Table.

| Compound | Solubility at 40° C. | Solubility of 0° C. |
| --- | --- | --- |
| Comp. I-1 | dissolved within 120 sec. | No deposition within 180 sec. |
| Comp. I-2 | dissolved within 150 sec. | No deposition within 180 sec. |
| Comp. I-4 | dissolved within 150 sec. | No deposition within 180 sec. |
| Comp. I-11 | dissolved within 120 sec. | No deposition within 180 sec. |
| Comp. I-12 | dissolved within 140 sec. | No deposition within 180 sec. |
| Comp. I-22 | dissolved within 140 sec. | No deposition within 180 sec. |
| Comp. a | some insoluble remained at 300 sec. | Not examined |
| Comp. b | some insoluble remained at 300 sec. | Not examined |
| Comp. c | dissolved at 200 sec. | Deposition found at 120 sec. |
| Comp. d | dissolved at 180 sec. | Deposition found at 150 sec. |

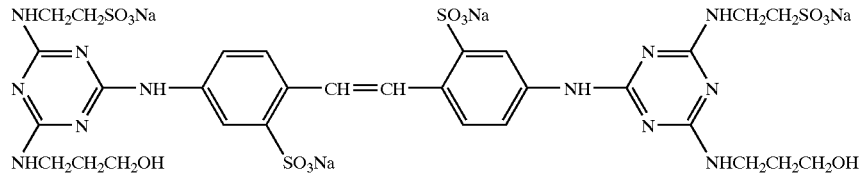

Comparison compound a

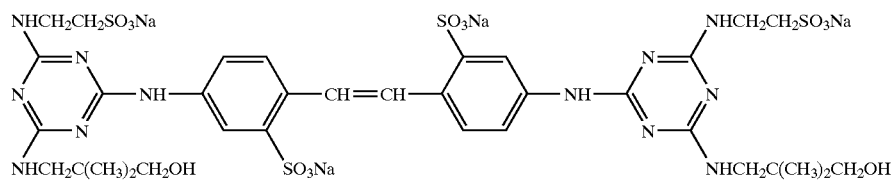

Comparison compound b

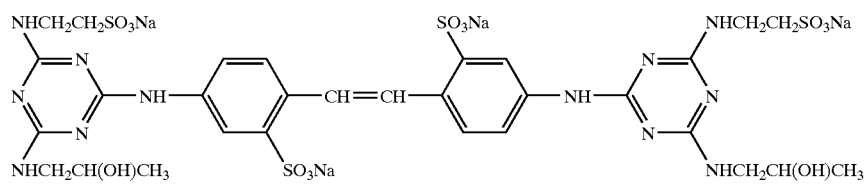

Comparison compound c
described in DE 1946316

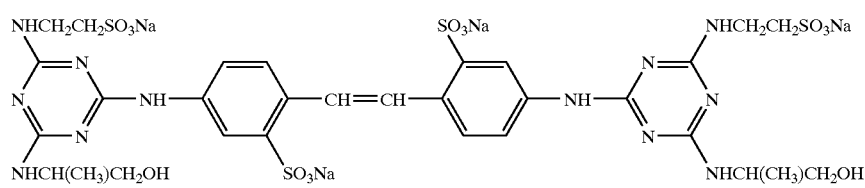

Comparison compound d
described in Japanese Patent Application No. 6-332127

EXAMPLE 8

In 1 mL of water was dissolved 10 mg of each of Compounds I-1, I-2, I-3, I-4, I-5, I-11, I-12, I-13, I-14, I-21, and I-22. The aqueous solution was diluted with methanol to give 5 mL of an aqueous methanol solution.

The resulting aqueous methanol solution was applied on to a filter paper sheet, and the paper sheet was dried. Thus treated filter paper sheet was irradiated with a UV light ($\lambda$254 nm). All paper sheets emitted blue fluorescence.

What is claimed is:

1. 4,4'-Bis(1,3,5-triazinylamino)stilbene-2,2'-disulfonic acid derivative having the following formula:

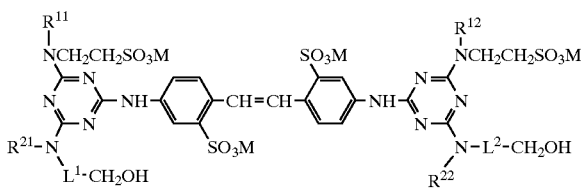

in which
each of $R^{11}$ and $R^{12}$ independently is hydrogen, methyl, ethyl, n-propyl, n-butyl, or 2-sulfoethyl;
each of $R^{21}$ and $R^{22}$ independently is hydrogen, methyl, ethyl, n-propyl, isopropyl, 2-hydroxyethyl, 2-hydroxypropyl, 3-hydroxypropyl, 2,3- dihydroxypropyl, 2-sulfoethyl, 2-(2-hydroxyethoxy)ethyl, 2-[2-(2-hydroxyethoxy)ethoxy]ethyl, phenyl, naphthyl, 4-hydroxyphenyl, 3,5-dicarboxyphenyl, 4-methoxyphenyl, and 3-isopropylphenyl;

each of $L^1$ and $L^2$ is an alkylene group having 2 to 8 carbon atoms, which alkylene group has one or more substituents selected from the group consisting of hydroxyl and hydroxyalkyl having 1 to 3 carbon atoms; and M is a hydrogen atom, an alkali metal atom, or pyridinium group.

2. 4,4'-Bis(1,3,5-triazinylamino)stilbene-2,2'-disulfonic acid compound of claim 1, wherein at least one of $L^1$ and $L^2$ is a divalent group which is represented by one of the following formulas 1) to 5):

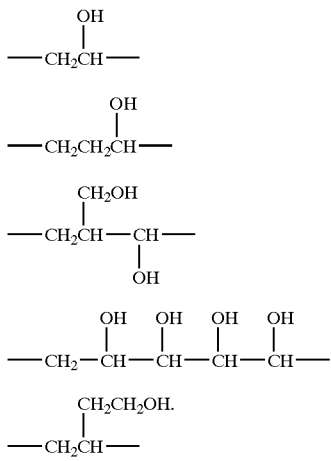

3. 4,4'-Bis(1,3,5-triazinylamino)stilbene-2,2'-disulfonic acid compound of claim 1, wherein at least one of $L^1$ and $L^2$ is a divalent group which is represented by one of the following formulas 1) to 4):

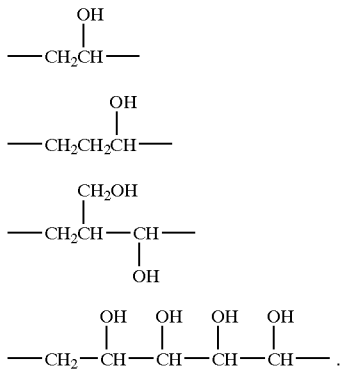

4. 4,4'-Bis(1,3,5-triazinylamino)stilbene-2,2'-disulfonic acid compound of claim 1, wherein each of $R^{11}$ and $R^{12}$ in the formula independently is a hydrogen or methyl.

5. 4,4'-Bis(1,3,5-triazinylamino)stilbene-2,2'-disulfonic acid compound of claim 1, wherein each of $R^{21}$ and $R^{22}$ in the formula independently is hydrogen, methyl, ethyl, isopropyl, 2-hydroxyethyl, 2-hydroxypropyl, 3-hydroxypropyl, 2,3-dihydroxypropyl, 2-(2-hydroxyethoxy)ethyl, 2-[2-(2-hydroxyethoxy)ethoxy]ethyl, phenyl, or 4-hydroxyphenyl.

6. An aqueous solution in which a 4,4'-Bis(1,3,5-triazinylamino)stilbene-2,2'-disulfonic acid compound having following formula is dissolved in water:

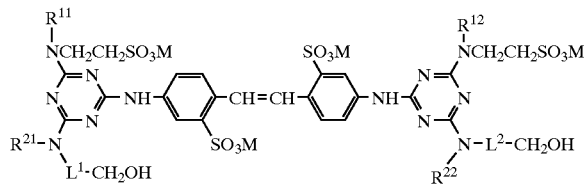

in which each of $R^{11}$ and $R^{12}$ independently hydrogen, methyl, ethyl, n-propyl, n-butyl, or 2-sulfoethyl;

each of $R^{21}$ and $R^{22}$ independently is hydrogen, methyl, ethyl, n-propyl, isopropyl, 2-hydroxyethyl, 2-hydroxypropyl, 3-hydroxypropyl, 2,3-dihydroxypropyl, 2-sulfoethyl, 2-(2-hydroxyethoxy)ethyl, 2-[2-(2-hydroxyethoxy)ethoxy]ethyl, phenyl, naphthyl, 4-hydroxyphenyl, 3,5-dicarboxyphenyl, 4-methoxyphenyl, and 3-isopropylphenyl;

each of $L^1$ and $L^2$ is an alkylene group having 2 to 8 carbon atoms, which alkylene group has one or more substituents selected from the group consisting of hydroxyl and hydroxyalkyl having 1 to 3 carbon atoms; and M is a hydrogen atom, an alkali metal atom, or pyridinium group.

7. A method of brightening a surface of material with fluorescence which comprises applying onto the surface an aqueous solution in which a 4,4'-Bis(1,3,5-triazinylamino)stilbene-2,2'-disulfonic acid compound having the following formula is dissolved in water:

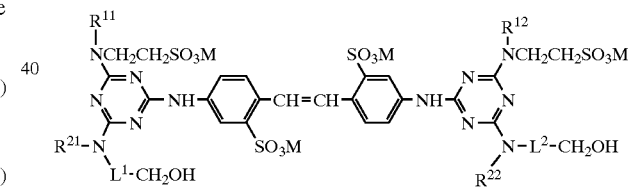

in which each of $R^{11}$ and $R^{12}$ independently is hydrogen, methyl, ethyl, n-propyl, n-butyl, or 2-sulfoethyl;

each of $R^{21}$ and $R^{22}$ independently is hydrogen, methyl, ethyl, n-propyl, isopropyl, 2-hydroxyethyl, 2-hydroxypropyl, 3-hydroxypropyl, 2,3-dihydroxypropyl, 2-sulfoethyl, 2-(2-hydroxyethoxy)ethyl, 2-[2-(2-hydroxyethoxy)ethoxy]ethyl, phenyl, naphthyl, 4-hydroxyphenyl, 3,5-dicarboxyphenyl, 4-methoxyphenyl, and 3-isopropylphenyl;

in each of $L^1$ and $L^2$ is an alkylene group having 2 to 8 carbon atoms, which alkylene group has one or more substituents selected from the group consisting of hydroxyl and hydroxyalkyl having 1 to 3 carbon atoms; and M is a hydrogen atom, an alkali metal atom, or pyridinium group.

* * * * *